United States Patent [19]

Murr

[11] 4,285,580
[45] Aug. 25, 1981

[54] COLOR VISION PERCEPTION TESTING DEVICE

[75] Inventor: William C. Murr, Piedmont, Calif.

[73] Assignee: Synemed, Inc., Berkeley, Calif.

[21] Appl. No.: 92,524

[22] Filed: Nov. 8, 1979

[51] Int. Cl.³ .......................... G03F 3/08; A61B 3/02
[52] U.S. Cl. .......................................... 351/35; 358/80
[58] Field of Search ................. 356/42 D; 351/32, 35, 351/36; 358/80

[56] References Cited

U.S. PATENT DOCUMENTS

| | | | |
|---|---|---|---|
| 3,801,188 | 4/1974 | Hunt et al. .......................... 351/35 X |
| 3,883,234 | 5/1975 | Lynn et al. .............................. 351/23 |

FOREIGN PATENT DOCUMENTS 7507263  10/1976  Fed. Rep. of Germany ............. 358/80

*Primary Examiner*—John K. Corbin
*Assistant Examiner*—Rodney B. Bovernick
*Attorney, Agent, or Firm*—Harris Zimmerman; Howard Cohen

[57] ABSTRACT

A controlled color source used in testing color vision perception includes a cathode ray tube capable of producing the three primary colors and at least one photo-detector array coupled directly to the tube screen for sensing the primary color output of the screen. The device also includes a microprocessor which processes the photo-detector signals and compares them with stored values having a predetermined correspondence to a desired color output of known hue, saturation, and luminance. The output of the comparison check is used to correct the drive voltage of the electron guns of the cathode ray tube, so that a precise color is displayed by the tube. A subject responds to the displayed color, and the color saturation and hue data are graphically displayed or stored for further use.

10 Claims, 1 Drawing Figure

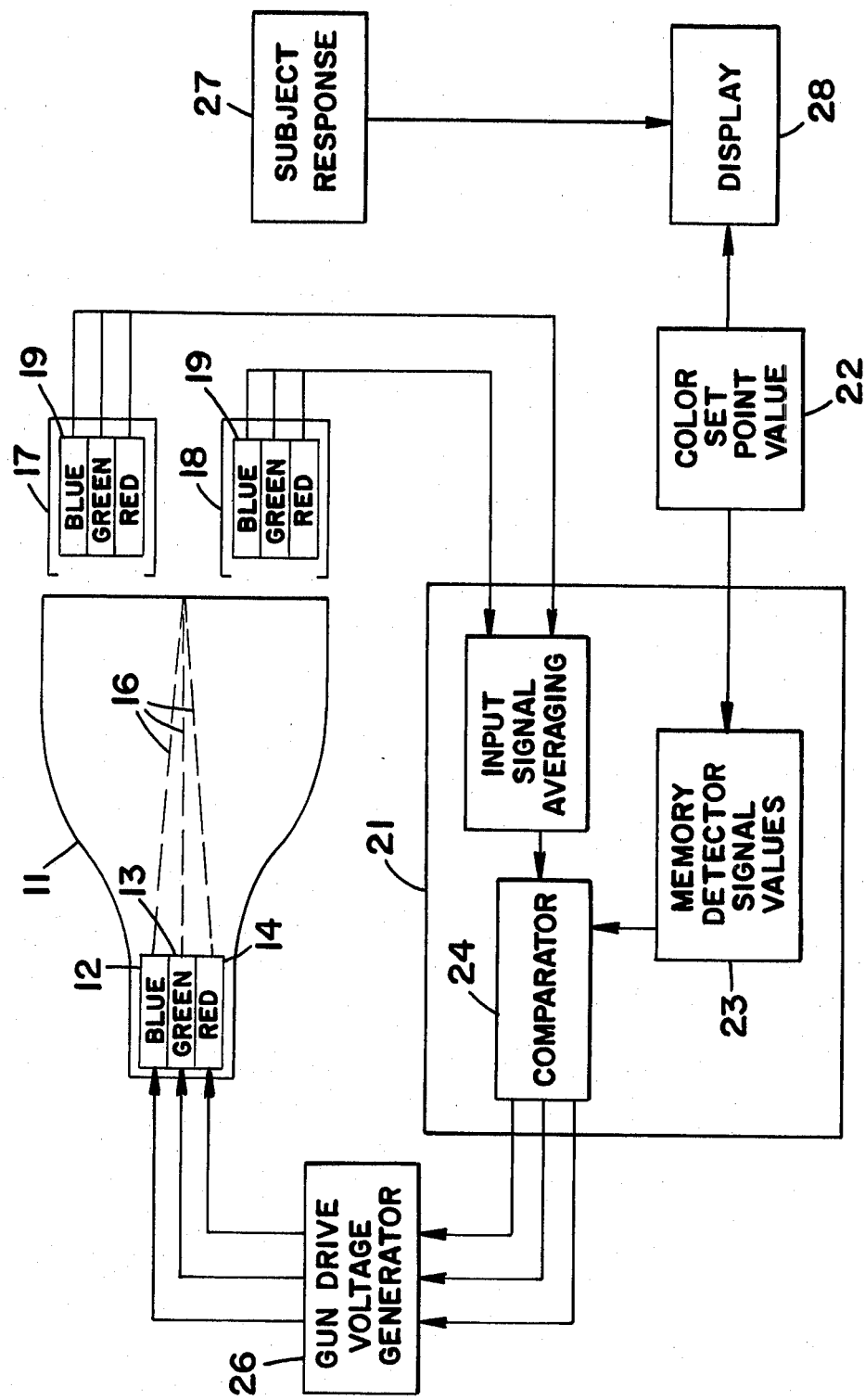

COLOR VISION PERCEPTION TESTING DEVICE

BACKGROUND OF THE INVENTION

The visual perception of color is known to be a highly subjective phenomenon, difficult to investigate empirically. This is due in part to the highly erratic response of subjects to color stimulus, because of complex psychological and physiological factors. It is also due to the rather inexact nature of the color perception testing procedures known in the prior art.

Most color vision testing procedures involve the use of dot matrices or color bar designs printed on display cards and shown to the test subject. In most testing procedures, the illumination of the display is not monitored for color value or intensity, nor are the ambient light conditions controlled. Other testing devices which employ illuminated color filter combinations are similarly errant in their lack of control of the lighting conditions of the examination. Furthermore, no device in the prior art is capable of maintaining a constant luminance level while varying the hue and saturation of the output signal.

SUMMARY OF THE PRESENT INVENTION

The present invention generally comprises a controlled color source useful in the precise examination and evaluation of color perception of a subject. The device generates a light output having precisely controlled hue, intensity, and saturation for the examination of color vision under exact, reproducible testing conditions. Thus color perception of a subject may be evaluated entirely objectively.

The device includes a cathode ray tube capable of emitting the primary colors, blue, green, and red, as well as any combination thereof. Affixed to the screen of the CRT is a pair of photodetector arrays. Each photodetector array includes a trio of photosensors, each responding to one of the primary colors.

The device of the present invention also includes a microprocessor which receives the outputs of the pair of photodetector arrays, and operates on those signals to average their values. A color set point value is put into the microprocessor, as by a predetermined program, and the microprocessor converts the color hue and saturation of the set point to a trio of photodetector signal values which correspond exactly to the color set point. The detector signal values of the set point are then compared to the average signal from the photodetector arrays. If the compared signal values are not within acceptable tolerances, the comparator generates a control signal to alter the drive voltage of the electron guns of the CRT, so that the average output of the tube screen matches the detector signal values of the desired color set point value.

The color set point value may also be put into a display or storage device, along with the response data of the subject viewing the CRT screen. This information may be displayed graphically, or stored for later evaluation. The graphic display may comprise a polar coordinate graph in which the angular variable corresponds to color value, and the radial variable corresponds to color saturation.

A BRIEF DESCRIPTION OF THE DRAWING

The FIGURE is a block diagram flow chart of the color perception evaluation device of the present invention.

A BRIEF DESCRIPTION OF THE PREFERRED EMBODIMENT

The present invention generally comprises a controlled color source for precisely evaluating visual color perception. With reference to the accompanying FIGURE, the apparatus includes a cathode ray tube 11 which is capable of emitting the three primary colors blue, green, and red, as well as any combination thereof. In the preferred embodiment depicted in the FIGURE, the CRT 11 is shown to include three electron guns 12, 13, and 14, each adapted to illuminate one of the primary color phosphors disposed on the screen 16 of the tube 11. It should be noted that the present invention may be adapted to employ a color CRT having a single electron gun, as is known in the prior art.

Affixed to the screen 16 of the color CRT 11 are a pair of photosensor arrays 17 and 18. Each array includes a trio of photodiodes 19, each of the photodiodes having a filtered input so that it responds to one of the three primary colors emitted from the screen 16. The arrays 17 and 18 preferably may be placed at diagonally opposed corners of the screen 16. Each of the diodes 19 of the arrays 17 and 18 generates a signal which is proportional to the intensity of the respective primary color to which it is sensitive. The arrays 17 and 18 thus monitor the color output of the screen 16 at two different locations thereof, and generate a signal which varies precisely according to the primary color output of the cathode ray tube.

The apparatus of the present invention also includes a microprocessor 21. As shown functionally in the FIGURE, the microprocessor 21 receives the primary color output signals from the photosensor arrays 17 and 18, and averages the signals to determine the average primary color output of the cathode ray tube. The signals from the arrays 17 and 18 may first be converted from analog voltage signals to digital signals by an appropriate A/D converter (not shown), or the analog signals may be converted to comparable digital information by the microprocessor 21.

The apparatus also includes a memory 22 which stores a plurality of predetermined color set point values. The memory 22, which may be under program control, provides a predetermined sequence of color set point values to the microprocessor 21. Each color set point value specifies a triplet of color saturation values, one for each of the primary colors.

Each of the color set point values called forth in the memory 22 is put into a memory 23. The memory 23 comprises a "map" which stores a triplet of desired detector signal values of the arrays 17 and 18, one triplet of detector signal values for each color set point value.

The microprocessor 21 also includes a functional comparator 24 which receives the average signal originating from the arrays 17 and 18, as well as the expected detector signal values from the memory 23. If the average signal value differs from the expected detector signal value by more than a predetermined minimum amount, the comparator 24 generates a control signal which is connected to the electron gun drive voltage generator 26. The signal from the comparator causes the gun drive voltage generator to correct the drive voltages applied to the electron guns 12–14 so that the color output of the screen 16 is substantially identical to the color set point values called forth by the memory 22. Thus a subject viewing the color output of the screen 16 will view a color display which corresponds precisely to the set point value called forth by the memory 22.

The signal averaging function and the signal comparing function may be performed for each new raster scan of the screen; i.e., 60 times per second. If the color output of the CRT 11 does not match the desired set point value, the error will be corrected apparently simultaneously with the initiation of the color display.

The present invention employs a pair of photosensor arrays so that errors generated by faults in the CRT electron gun convergence, magnetization, or the like may be detected. The provision of the two photosensor arrays at different portions of the screen also permits the present invention to present two precisely controlled color displays in split screen fashion.

One possible examination technique for visual color perception comprises the initial display of pure white light by the CRT 11. A predetermined sequence of color set point values from the memory 22 is then called forth to increase gradually the color saturation of a particular color, so that the CRT display will gradually change from white to an increasing saturation of a particular color while the luminance remains constant. When a test subject first discerns that the white CRT output has changed to a particular color output, the subject actuates a response device 27, such as a push button switch or the like. The color set point value displayed at the moment the subject response device is actuated is fed to a display device 28. The display device may comprise a polar coordinate graphic output in which the angular variable corresponds to the color spectrum, and the radial variable corresponds to percentage color saturation. Alternatively, the display 28 may be replaced by a memory which stores the data concerning the threshold response of the subject to particular color saturation values.

The preferred embodiment of the present invention may be realized through the use of a microprocessor such as the PDP-11, or an 8080, both known in the prior art. These devices may be employed in conjunction with 30 K bytes of read-only memory, as is also known in the prior art. Of course, other microprocessor devices and memories may be employed by those skilled in the art.

The present invention as described in the foregoing preferred embodiment may also be employed to display characters or symbols on the CRT screen 16. In this alternative embodiment a video character generator microcircuit may be employed in conjunction with the microprocessor 21, and the correct electron gun drive voltage values corresponding to one or more color set point values may be stored briefly in the microprocessor memory. When a character or symbol is to be displayed at a particular color set point value, the stored voltage values may be recalled so that the character is presented on the screen 16 with the precise, pre-determined color value.

It should be noted that the memory 23 which stores the desired detector signal values is preprogramed with detector signal values which emanate from a calibrated color source. Thus the examinations of visual perception of color performed with the present invention are reproducible with great precision, a precision extending directly from a calibrated color source. Thus the erratic testing procedures for visual color perception known in the prior art are obviated by the uniformity and standardization made possible by the present invention.

I claim:

1. An apparatus for producing a controlled color light signal, comprising a light source capable of producing and displaying any combination of the three primary colors; photodetector means for sensing the primary color output of said light source and generating a detector signal in response thereto; first storage means for storing a plurality of predetermined detector signal values corresponding to a unique combination of specific color output values of said light source; comparator means for comparing said detector signal with one of said stored detector signal values corresponding to a desired specific color output of said light source, and for generating a comparator signal in response to differences therebetween; and control means for receiving said comparator signal and correcting the output of said light source in response thereto to display said unique combination of color output values.

2. The apparatus of claim 1, wherein said light source comprises a cathode ray tube.

3. The apparatus of claim 2, wherein said control means includes the drive voltage generators of the electron guns of said cathode ray tube.

4. The apparatus of claim 1, wherein said photodetector means includes a trio of photodiodes, each filtered to respond to a respective one of the three primary colors.

5. The apparatus of claim 2, wherein said photodetector means includes a pair of photosensor arrays, each directed at differing portions of the screen of said cathode ray tube.

6. The apparatus of claim 1, further including a second means for storing a plurality of color set point values, each comprising a desired specific color output of said light source, said second storage means providing said set point values to said first storage means in a predetermined sequence.

7. The apparatus of claim 6, further including subject response means for recording the threshold color saturation responses of a subject viewing said light source to said color set point values.

8. The apparatus of claim 7, further including graphic display means for plotting said threshold responses of said subject with respect to said color set point values.

9. The apparatus of claim 1, wherein said comparator means includes limiter means to squelch said comparator signal when said differences fall below a predetermined amount.

10. The apparatus of claim 1, wherein said predetermined detector signal values are provided by a calibrated color source.

* * * * *